United States Patent [19]

Bernofsky

[11] Patent Number: 5,804,443
[45] Date of Patent: Sep. 8, 1998

[54] HUMAN MONOCYTIC LEUKEMIA CELL LINE

[76] Inventor: Carl Bernofsky, 6478 General Diaz St., New Orleans, La. 70124

[21] Appl. No.: 808,201

[22] Filed: Feb. 28, 1997

[51] Int. Cl.$^6$ ..................................................... C12N 5/00
[52] U.S. Cl. ........................................ 435/372.1; 435/372
[58] Field of Search ................................. 435/372, 372.1

[56] References Cited

U.S. PATENT DOCUMENTS 5,272,082  12/1993  Santoli et al. ........................ 435/372.3

OTHER PUBLICATIONS

Atkinson, *Cellular Energy Metabolism and Its Regulation*, Academic Press, New York, 1977.

Bernofsky et al., "Latency of Adenosine 5'-Triphosphate in MC-1010 Cells," *Biochemical Archives* 9:51–64 (1993).

Bernofsky et al., "Spin trapping endogenous radicals in MC-1010 cells: Evidence for hydroxyl radical and carbon-centered ascorbyl radical adducts," *Molecular and Cellular Biochemistry* 148:155–164 (1995).

Counter et al., "Telomerase activity in human ovarian carcinoma," *Proc. Natl. Acad. Sci.* 91:2900 (1994).

Harlow and Lane, *Antibodies: A Laboratory Manual* (Cold Spring Harbor, Cold Spring Harbor, N.Y., 1988).

Holmsen and Dangelmaier, "Measurement of Secretion of Adenine Nucleotides," *Meth. Enzymol.* 169:195 (1989).

Lange et al., "Growth Factor Requirements of Childhood Acute Leukemia: Establishment of GM–CSF-Dependent Cell Lines," *Blood* 70(1):192–199 (1987).

Lundin, "Analytical Applications of Bioluminescence: The Firefly System," *Clinical and Biochemical Luminescence* (Kricka and Carter, ed.), Marcel Dekker, New York, 1982, p. 43.

O'Connor et al., "Growth Factor–Dependent Differentiation Along the Myeloid and Lymphoid Lineages in an Immature Acute T Lymphocytic Leukemia," *J. Immunol.* 145:3779 (1990).

Santoli et al., "Synergistic and Antagonistic Effects of Recombinant Human Interleukin (IL) 3, IL–1α, Granulocyte and Macrophage Colony–Stimulating Factors (G–CSF and M–CSF) on the Growth of GM–CSF–Dependent Leukemic Cell Lines," *The Journal of Immunology* 139(10):3348–3354 (1987).

Santoli et al., "Synergistic and Antagonistic Effects of IL–1α and IL–4, Respectively, on the IL2–Dependent Growth of a T Cell Receptor–γδ$^+$ Human T Leukemia Cell Line," *J. Immunol.* 144:4703 (1990).

Stanley, "Extraction of Adenosine Triphosphate from Microbial and Somatic Cells," *Meth. Enzymol.* 133:14 (1986).

Tang et al., "Isolation of a Novel Atpase From Leukemic Monocytes," *FASEB J.* 7:A717 (1993).

Wulff and Doppen, "Luminometric Method," in *Methods of Enzymatic Analysis*, 3 ed., vol. 7 (Bergmeyer, Bergmeyer, and Graβl, ed.) VCH Pub., Weinheim, 1985, p. 357.

Chang et al. (1975) Biochem. Biophys. Res. Comm., 64(2), "Correlation Between DNA Synthesis and Intracellular NAD in Cultured Human Leukemic Lymphocytes", pp. 539–545.

Sombrook et al. (1989) Molecular Cloning A Laboratory Manual, 2md Edn., Cold Spring Harbor Laboratory Press, pp. xxxii–xxxv.

*Primary Examiner*—Jon P. Weber
*Attorney, Agent, or Firm*—McDonnell Boehnen Hulbert & Berghoff

[57] ABSTRACT

The present invention comprises a novel immortal human monocytic leukemia cell line, designated MC-1010. This cell line has been demonstrated to induce an immune response when injected into non-human primates. This leukemic cell line is also a source of a unique ATPase that is found in only low levels in normal human cells. The immortal nature of the MC-1010 cell line allows it to be used as the replicative fusion partner for making hybridomas and also makes it an excellent source of enzymes (e.g., telomerase) and other cellular components involved in the cellular replication process.

3 Claims, No Drawings

HUMAN MONOCYTIC LEUKEMIA CELL LINE

BACKGROUND OF THE INVENTION

1. Field of the Invention

The present invention relates to the field of immortal human monocytic leukemia cells.

2. Summary of the Related Art

Human leukemic cells are generally very difficult to proliferate in vitro. Leukemic colonies usually undergo terminal differentiation, and subculturing is usually not successful for more than two or three passages.

Nevertheless, there have been a number of reports of established leukemic cell lines. Santoli et al. (U.S. Pat. No. 5,272,082) disclosed two cytotoxic acute T lymphoblastic leukemia cell lines. These cell lines displayed a higher cytotoxic efficiency as compared to other continuous cell lines established by Santoli et al., *J. Immunol.* 144 4703 (1990) and O'Connor et al., *J. Immunol.* 145, 3779 (1990) as well as lymphokine-activated killer cells from normal donors. Santoli et al., *J. Immunol.* 139, 3348 (1987), and Lange et al., *Blood* 70, 192 (1987), disclosed three GM-CSF-dependent human leukemia cell lines.

Despite what progress has been made, we are still a very long way from understanding human leukemia and from developing both completely safe and effective treatments. Accordingly, there remains a need for additional tools in the fight against leukemia.

SUMMARY OF THE INVENTION

The present invention provides a novel human monocytic leukemia cell line, designated MC-1010, which is an important tool for investigating the mechanism and physiology of human leukemia. This cell line has been demonstrated to induce an immune response when injected into primates. This leukemic cell line is also a source of a unique ATPase that is found in only low concentrations in normal human cells. The immortal nature of the MC-1010 cell line allows it to be used as the replicative fusion partner for generating hybridomas and makes it an excellent source of enzymes and other cellular components involved in the cellular replication process.

The foregoing merely summarizes certain aspects of the present invention. It is not intended, nor should it be construed, as limiting the invention in any way. All patents and other publications cited herein are hereby incorporated by reference in their entirety.

DETAILED DESCRIPTION OF THE INVENTION

The present invention comprises a novel human monocytic leukemia cell line, designated MC-1010. The cell line was obtained from a 25-year old Caucasian male who had just been diagnosed with acute monocytic leukemia, as described more completely in Example 1, infra, and reported in Chang and Bemofsky, *Biochem. Biophys. Res. Commun.* 64, 539 (1975). The MC-1010 cell line was deposited in accordance with the Budapest Treaty with the American Type Culture Collection (ATCC), 12301 Parklawn Drive, Rockville, Md., 20852 (U.S.A.), an accepted Depository Authority, on Dec. 24, 1996 and given the designation ATCC CRL-12253.

MC-1010 cells have a variety of uses. One of their most significant uses is as a research tool for scientists and physicians investigating leukemia, both in the laboratory and clinically. As described in Example 2, infra, MC-1010 cells are capable of inducing a protective immune response in non-human primates injected with the cells.

MC-1010 cells also can be used as a model system to investigate the mechanisms that control the in vivo growth of human monocytic leukemic cells. They can be used to study the interactions of hemopoietic growth or differentiation factors and their effects on cell proliferation and terminal differentiation.

One major utility of an immortalized monocyte cell line is as a source of a homogeneous monocyte population. A homogeneous monocyte population can be used as a biological control during cell sorting, including and not limited to flow cytometry, in affinity purification, and as size markers in histological preparations of tissues or cells to be viewed under light, UV, or scanning electron microscopy. An immortalized monocyte cell line is useful as a source of homogeneous cells for producing specific cytokines in response to appropriate stimulation. It also allows for the specific biochemical characterization of monocyte cells, and is a readily available source of homogeneous cells that allows for controlled replication of chemical assays and other forms of biological testing. A homogeneous monocyte cell line is a useful source of leukemic DNA, mRNA, enzymes, subcellular organelles, and antigens.

Because of their immortal nature, MC-1010 cells can be used as a replicative fusion partner together with antibody-producing B lymphocytes to generate hybridomas for the production of human monoclonal antibodies and cytokines. Hybridoma technology is an established art, and MC-1010 cells can be used in accordance with standard methods well known to those skilled in the art to establish hybridoma cell lines [Harlow and Lane, *Antibodies: A Laboratory Manual* (Cold Spring Harbor Laboratory, Cold Spring Harbor, N.Y., 1988)].

The immortal nature of MC-1010 cells also makes them an excellent source of enzymes involved with replication, such as telomerase [Counter et al., *Proc. Nat. Acad. Sci.*, 91, 2900 (1994)], components of the DNA polymerase complex, and other ATPases uniquely associated with the replication process. Such cellular components can be harvested using standard methods.

The MC-1010 cell line is also useful for developing specific probes for the detection of MC-1010 and related cells by in situ hybridization techniques and, therefore, for the diagnosis of related leukemias. Such probes can be, for example, oligonucleotides complementary to unique MC-1010 nucleic acid sequences. Alternatively, a probe can be an MC-1010-specific antibody. In any case, standard techniques can be employed to detect the probe and, hence, the MC-1010 cell. For example, the oligonucleotide can be radiolabeled, or the antibody probe can be labeled with biotin and detected via enzyme-linked immunoassay. These and other techniques are well known to those skilled in the art.

MC-1010 cells are a useful source of three novel ribonucleoproteins (designated ATPase I, II, and III) that have ATPase and nuclease activity [Bemofsky and Tang, *Biochem. Arch.* 9, 51 (1993)]. Fractionation of monocytes and other leukocytes from normal donors by gradient centrifugation has revealed that, on a cellular basis, normal cells contain only about 2% of the ATPase activity present in MC-1010.

The ATPases from MC-1010 cells are unusual in that they are extracted with perchloric acid under conditions ordinarily used to prepare acid-soluble components from cells. The enzymes can be separated by electrophoresis on native polyacrylamide gels and identified by means of a specific stain for ATPase activity.

The ATPases contain $^{35}S$ when prepared from cells grown in the presence of [$^{35}S$]methionine and are sensitive to inactivation by proteinase K; thus, they are not ribozymes. Nevertheless, they are dependent on the presence of RNA because treatment with RNAse results in the loss of ATPase activity as well the loss of silver-staining ability. These characteristics, and the solubility of these enzymes in perchloric acid, appear to reflect their content of RNA. UV-irradiation of MC-1010 cells results in increased levels of ATPase activity, suggesting that these enzymes may have a role in DNA repair.

Their method of preparation indicates that the ATPases may be subunits of larger enzyme complexes. The smallest of the ATPases has an apparent molecular weight of about 6 kD; the molecular weight of the other ATPases is substantially larger. ATPase activity is likely associated with a larger complex, because when the [$^{35}S$]methionine-labeled ATPases were cut from a native gel and reanalyzed on an SDS gel, all three radioactive bands had the same electrophoretic mobility. It has also been determined that ATPase I (the 6 kD enzyme) has no nuclease activity, whereas ATPase III (the high molecular weight enzyme) is a potent nuclease.

An ATPase activity stain, based on the lead precipitation of phosphate released from ATP followed by the conversion of lead phosphate to the dark sulfide, suggested that nucleic acid associated with the ATPases, and co-staining with them, is responsible for the silver-staining activity. The presence of nucleic acid is supported by the finding that, when the ATPases were extracted from MC-1010 cultured in the presence of [$^{32}P$]inorganic phosphate, all of the bands that were silver stained were also highly labeled with $^{32}P$.

In another experiment designed to confirm the presence of protein in the ATPases, MC-1010 was cultured in the presence of [$^{35}S$]methionine, and the enzymes were extracted and subjected to electrophoresis and staining for ATPase activity. Autoradiography of the gel showed a coincidence of the activity stain with the spot caused by the radioactive amino acid. This result, and their sensitivity to Proteinase K, confirms that the ATPases are not ribozymes.

Studies have been conducted using a [$^{32}P$]5'-labeled 17-mer oligonucleotide (pUC/M13 Forward (−40) 17 mer) annealed to single-stranded DNA (from M13mp18 bacteriophage) containing complimentary sequences, and no evidence was found that the ATPase was associated with helicase activity. However, the ATPase could degrade the radioactive 17-mer to a [$^{32}P$]5'-labeled nucleotide product, and all 17 [$^{32}P$]5'-labeled intermediates were observed. Although every phosphodiester linkage in the 17-mer was vulnerable to nuclease activity, there appeared to be preferred sequences because the early products of the reaction were dominated by several intermediates of moderate length. The ATPases can also hydrolyze [$^{32}P$]5'-labeled double-stranded DNA. Interestingly, the nuclease activity could be completely inhibited by any of the ribonucleoside and deoxyribonucleoside triphosphates, but not by the monophosphates. This could be simple competitive inhibition. The ATPases are also inhibited by RNAse.

To determine if the above ATPases are also present in normal leukocytes, monocytes, lymphocytes, and neutrophils from the blood of normal donors were isolated and examined for perchloric acid-extractable ATPase. ATPase activity of the normal leukocytes was only 2.2±2.2% (mean ± SD, n=8) of the activity found in MC-1010 when measured on a comparable cellular basis. This activity was too small to be observed on gels, but it could be measured by the more sensitive (though less specific) technique of luminometry. The near absence of these ATPases from normal monocytes and other white blood cells suggests that the ATPases may be unique to leukemia cells, which warrants further study. Currently, the MC-1010 cells of the present invention are the only known source of these ATPases.

MC-1010 cells can also be used as a sensitive test system for monitoring the presence of environmental substances that may have adverse health effects on human cells. Appropriate measurements of adenine nucleotides are used as a risk-assessment biomarker.

The use of adenine nucleotides as biomarkers for the assessment of genotoxic agents is based on the fact that damage to DNA leads to activation of poly(ADP-ribose) polymerase, an enzyme that catalyzes the conversion of $NAD^+$ to polymers of ADP-ribose that are linked to chromosomal proteins. The formation of poly(ADP-ribose) is believed to assist in the process of DNA repair. It also leads to the release of nicotinamide which is quickly recycled to $NAD^+$ by a process that requires 2 mol of ATP. The net effect is that formation of poly(ADP-ribose) occurs at the expense of ATP, whose depletion can serve as an early indicator of DNA damage.

MC-1010 and other human cells that grow continuously in tissue culture can be used to assess the presence of agents that lead to the net loss of adenine nucleotides. These agents can be chemical substances incorporated into the culture medium, or physical conditions present in the surrounding environment. When MC-1010 is used for this purpose, the cells are maintained under standardized conditions by periodic replacement of medium at a frequency that keeps the concentration of nutrients, by-products, and cells relatively constant. This creates a laboratory approximation of the physiological steady state.

Under steady state conditions, the intracellular level of adenine nucleotides in a control culture is predictable and constant over a defined measurement period and reflects the metabolic status and vitality of the cells. This relationship derives largely from the fact that the relative and absolute concentrations of the three adenine nucleotides (ATP, ADP, and AMP) are key elements in the regulatory mechanism that determines the ability of the cell to meet its energy requirements. On one hand, ATP is the common energy source for essentially all energy-requiring life processes, including cell division, and on the other, the provision of ATP is the principal objective of the central oxidative pathways of intermediary metabolism. The role of coordinating these major metabolic activities in the cell makes the adenine nucleotide system an important biomarker.

Both synthesis and utilization of ATP are influenced by nutrient availability, growth cycle status, and other intrinsic and environmental factors. In addition, ATP is regulated by the action of intracellular adenylate kinases. The latter are enzymes that continuously equilibrate the adenine nucleotides in a manner best represented in terms of energy charge, a ratio defined as $\{[ATP]+\frac{1}{2}[ADP]\}/\{[AMP]+[ADP]+[ATP]\}$. The derivation and significance of the energy charge expression is common knowledge (Atkinson, *Cellular Energy Metabolism and Its Regulation*, Academic Press, New York, 1977). The energy charge ratio describes that portion of cellular adenine nucleotides that is available for energy-requiring processes. However, energy charge alone does not reveal the true extent of energy resources available to a cell; one must also know the absolute cellular quantity of the adenine nucleotides. The requisite information is adequately contained in the associated values for energy charge (a decimal number between 0 and 1) and total adenine nucleotide content (generally 1 to 10 pmol/$10^3$ cells).

In practice, a substance being tested for potential genotoxic activity would be incorporated into the medium used by a cell culture which is then sampled and analyzed for its adenine nucleotide content an the identical manner as a parallel, untreated control culture. Because the method monitors a vital biomarker under stringent laboratory conditions, it could also be used for evaluating the metabolic response of human cells to a host of environmental variables. These would include atmospheric composition and pressure, electromagnetic fields, radioactivity, temperature, light of differing wavelengths, the presence of solid objects (ie. asbestos), and the effect of protective substances.

The present use of MC-1010 cells for evaluating DNA-damaging agents emphasizes the measurement of all three adenine nucleotides. The measurement of ATP alone is insufficient because intracellular adenine nucleotides are rapidly equilibrated by adenylate kinase, and a change in one is balanced by changes in the others. For example, a decrease in ATP might simply indicate the presence of a metabolic inhibitor instead of reflecting a response to DNA damage. The present usage, whereby all three adenine nucleotides are measured, clearly distinguishes between these two circumstances. Thus, a decrease of ATP in response to a metabolic inhibitor would be balanced by comparable increases in ADP and AMP, coupled with a sharp decline of energy charge, whereas the loss of ATP in response to DNA damage would be reflected by a net loss of all adenine nucleotides and a moderated decline of energy charge.

The extraction of adenine nucleotides from cells and their assay by the sensitive technique of luminometry is an established art [Lundin, in *Clinical and Biochemical Luminescence* (Kricka and Carter, ed.), Marcel Dekker, New York, 1982, p. 43, Wulff and Doppen, in *Methods of Enzymatic Analysis*, 3 ed., vol. 7 (Bergmeyer, Bergmeyer, and Graβl, ed.), VCH Pub., Weinheim, 1985, p. 357, Hampp, ibid., 370, Stanley, *Meth. Enzymol.* 133, 14 (1986), Holmsen and Dangelmaier, *Meth. Enzymol.* 169, 195 (1989)]. However, this art has been improved and optimized for MC-1010 cells (Bemofsky and Tang, supra). The improvements are based on the identification of previously unrecognized sources of error and the development of techniques for their elimination. The improved methods described by Bemofsky and Tang, supra are universally applicable and are intended to be utilized for the measurement of adenine nucleotides as described in the present application.

MC-1010 cells are preferably propagated in the following medium: RPMI-1640 (400 ml), heat-inactivated fetal bovine serum (100 ml), 0.1M BES/0.1M HEPES (Na$^+$), pH 7.5 (50 ml), and penicillin (10,000 units/ml)/streptomycin (10,000 μg/ml) (5 ml). BES=N,N-bis(2-hydroxyethyl)-2-aminoethanesulfonic acid; HEPES=N-(2-hydroxyethyl)piperazine-N'-(2-ethanesulfonic acid).

MC-1010 cells are maintained in stationary suspension culture (Petri dishes) at 36° C. (MC-1010 is sensitive to temperatures >38° C.) in a humidified atmosphere of 95% air/5% $CO_2$. Under these conditions, the cells form large aggregates and do not adhere to the glass. The usual viability is 90 to 94% and the doubling time about 48 hr. After doubling, the medium should be changed completely because of growth inhibitors that appear to accumulate in the medium. Attempts to supplement the culture with fresh medium (50%) or reuse the medium after adjusting the pH with 0.1M NaOH/0.1M NaHCO$_3$ have not been successful. The presence of lysed cells also has an adverse effect on cell viability. MC-1010 can be grown successfully in shake culture (50 rpm) in 500-ml side-arm flasks with a decrease in generation time but also with some loss of viability (86 to 90%).

Under optimum growth conditions, cell densities of 2 to 4×$10^6$ cells/ml can be continuously sustained and densities of 6×$10^6$ cells/ml readily obtained. However, excessive cell densities are inhibitory to growth, as are very low seeding densities.

During active growth, the cells assume a variety of shapes but are mainly oval and have a major pseudopod at one pole and "whiskers" at the other. Filamentous projections are readily observed with the light microscope, and these may be as long as the cells themselves. These structures may be related to the invasive character of the cells from which MC-1010 was derived. A small proportion of the culture consists of cells that are several times the size of the general population; this may reflect the polyploidy observed in chromosome studies.

In the absence of growth medium, when the cells are disturbed by an inhibitory substance, or when viability declines, the filaments and pseudopod disappear and the cells become uniformly spherical. From electron micrographs of glutaraldehyde-fixed cells, MC-1010 has a diameter of 8 to 15 microns and contains a large number of lipid bodies. Electron microscopy also reveals the presence of crystalloid elements and clusters of spherical particles.

MC-1010 contains a full complement of 46 chromosomes, none of which exhibits visible abnormalities. Of 100 metaphase MC-1010 spreads that were examined, 95 were diploid and 5 were tetraploid. The large cells present in MC-1010 cultures may represent cells with the tetraploid chromosome condition.

The presence of buffer significantly improves the performance of the culture medium with MC-1010 cells (which are sensitive to acid conditions), but a high concentration of HEPES buffer is somewhat inhibitory. For this reason, a mixture of two organic buffers, BES (pK 7.1) and HEPES (pK 7.5), in final concentrations of about 9 mM each, has been successfully used. The procedure for preparing the buffer mixture is given below. Note that the purity of these buffers has increased over the years, lessening the need for decolorization; also, the recent availability of their sodium salts may lead to a simpler method of preparation.

To make 250 ml of a 10X buffer solution, place 80 ml of water in a 400-ml beaker with a stirring bar, add 53.32 gm (0.25 mol) of BES and 59.58 gm (0.25 mol) of HEPES, and stir with mild heat until dissolved. Cool to room temperature (pH=ca. 5.1), and adjust to pH 7.8 with approximately 60 ml of 5M NaOH. This should be done in two stages with overnight (refrigerated) storage because of slow equilibration. Dilute the buffer to 250 ml (cylinder), decolorize by stirring 15 min with 5 to 10 cc of acid-washed charcoal, and filter through a 0.45-μm membrane (Millipore) covered with a thick fiberglass pre-filter. Re-check the pH; if too high, it can be adjusted with a (decolorized) solution of 1M BES/1M HEPES, pH 5.1.

Sterilize the 10X stock solution by filtration through a 0.22-μm membrane and keep refrigerated. To prepare a working solution, add 50 ml of stock to 450 ml of water and resterilize. The pH drops upon dilution. The final buffer (0.1M BES/0.1M HEPES/0.12M Na$^+$) is essentially isotonic and should be pH 7.5.

The MC-1010 cells of this invention may be modified by means of conventional recombinant genetic engineering techniques to confer other characteristics to the cell line to expand its research and therapeutic uses. Such techniques are described in standard texts, for example, Sambrook et al., *Molecular Cloning. A Laboratory Manual* (2nd ed., Cold Spring Harbor Laboratory, Cold Spring Harbor, N.Y., 1989). The present invention includes such genetically modified MC-1010 cells lines and cell lines derived therefrom.

The following Examples are for illustrative purposes only and are not intended, nor should they be construed, as limiting the invention in any way. Those skilled in the art will readily appreciate that modifications and variations can be made without exceeding the spirit or scope of the invention.

EXAMPLES

Example 1

Isolation of MC-1010 cells

Blood (30 cc) was drawn Nov. 5, 1974 from a 25-year old Caucasian male who had just been diagnosed with acute monocytic leukemia (Schilling variety) and had not yet received chemotherapy. The blood was drawn into a heparinized, plastic syringe, and erythrocytes were allowed to settle by gravity. The leukocyte-rich plasma was expelled through a bent needle, diluted with an equal volume of 0.9% NaCl, layered in 5-ml aliquots on 5 ml of a 10:24 mixture of 33.1% sodium Metrizoate (Gallard-Schlesinger, Carle Place, N.Y.), and 9.0% Ficoll (Pharmacia Fine Chemicals, Piscataway, N.J.) (final density=1.077 g/ml), and centrifuged at room temperature for 30 min at 400×g. The leukocytes, which formed a band above the interface, were removed, diluted with 0.9% NaCl, centrifuged as above for 10 min, washed with Hanks' balanced salt solution, resuspended in culture medium, and transferred directly to a spinner culture vessel.

The culture medium consisted of 80% RPMI-1640 and 20% heat-inactivated (56° C., 30 min) fetal calf serum and was supplemented with penicillin (100 units/ml) and streptomycin (100 μg/ml). The cells were stirred slowly at 37° C. in closed vessels under a gas phase of 95% air/5% $CO_2$, and fresh medium was added as necessary to maintain a concentration of 2–4×10$^6$ cells/ml. Cells were counted with a hemacytometer.

Cells were considered established after 4 weeks in culture and were frozen Jan. 15, 1975 (Freeze #1). Cells from Freeze #1 were subsequently rejuvenated May 20, 1976, cultivated for approximately 15 doublings, and refrozen Jul. 9, 1976 (Freeze #2). Tests for mycoplasma in cells rejuvenated from Freeze #2 were negative.

Under optimum growth conditions, the cells exhibit robust growth with greater than 90% viability and a doubling time of under 48 hours. Cells from Freeze #2 have been grown for periods of up to 41.6 months (approximately 633 doublings) with no signs of growth abatement.

Example 2

Induction of Anti-MC1010 Response

A healthy male chimpanzee (115 lb) was transfused under anesthesia via arm vein on each of days 1, 17, and 44 with 2.1×10$^9$ MC-1010 cells (88% viability) in 23 ml of serum- and antibiotic-free medium (RPMI-1640 supplemented with 0.1 vol of 0.1M BES/0.1M HEPES, pH 7.4), followed by 500 ml of 5% glucose. Blood was periodically collected for clinical evaluation and antibody testing. By day 58, the serum was highly cytotoxic to MC-1010 cells, and fractionation on Sephadex G-200 showed that cytotoxicity was associated with gamma-globulin. Similar boosters (6 ea) were continued at approximately six 2-week intervals, and antiserum collected another 8.5 months after the last booster. Throughout the 18.5-month study, the animal failed to develop leukemia and showed no outward signs of illness as a result of this challenge.

Example 3

Freezing and Thawing of MC-1010 Cells

Cryopreservative was prepared just prior to use by adding 25 ml of dimethylsulfoxide (DMSO, Spectrograde) to 75 ml of complete culture medium and mixing until the Schlieren pattern disappeared. The mixture, warm from dilution of the DMSO, was allowed to cool to room temperature then filter-sterilized and chilled on ice.

Ampoules (5-ml Wheaton pre-scored "Cryules") were labeled with ceramic marking ink fired into the glass with a Bunsen burner, and sterilized by autoclaving. Before and after the heat sealing process, the ampoules were chilled in an aluminum block kept on crushed ice. For heat sealing, the ampoules were held in one hand with a grip fashioned from a glass rod and rubber tubing while they were pull-sealed with a narrow flame.

Freeze #2 was prepared from actively-growing cells (shake culture) that were resuspended in fresh medium and chilled on ice. Ampoules were processed in groups of eight. Each ample received 2 ml of culture (3.6×10$^7$ MC-1010 cells) followed by 2 ml of cryopreservative (12.5% DMSO final concentration) and was kept cold for a total of 20 minutes with frequent swirling. The ampoules were heat sealed, chilled again, clamped (rubber bands) between two fitted Styrofoam blocks, wrapped in aluminum foil, and placed at a 30° angle in a −80° C. freezer for 24 hours. The ampoules were transferred to canes chilled on Dry Ice, then totally immersed in liquid nitrogen. MC-1010 cells from Freeze #2 bear the label "MC-1010 July, 1976" fused into the glass and were distributed between two liquid nitrogen storage Dewars.

For thawing, a frozen vial was placed in a small zip-lock plastic bag together with several ml of 70% ethanol, plunged into a 37° C. water bath using rubber-covered tongs, and transferred to ice as soon as the vial was thawed. The vial was wiped with 70% ethanol, snapped open using gauze sponges to protect the hands, and placed in an aluminum block kept on ice. Each 2 ml of cell suspension was transferred to 20 ml of cold, complete medium in a 50-ml centrifuge tube and kept on ice for 30 min with frequent swirling (MC-1010 is sensitive to DMSO at room temperature).

The cells were sedimented by gentle centrifugation (i.e., 500 rpm for 12 min), the supernatant removed by pipette, and the cells resuspended with 10 ml of cold medium, kept on ice for another 30 minutes with occasional swirling, and re-sedimented. This step was then repeated. Finally, the sedimented cells were resuspended with 7 ml of medium at room temperature, a sample taken for counting, and the remainder transferred to a 60-mm Petri dish and incubated.

At this point, the viability has been as low as 70%. The medium was replaced daily and the culture gradually expanded into multiple 100-mm Petri dishes until it became stabilized, at which time the culture was split every other day (or minimally, three times a week). MC-1010 was routinely cultured in Pyrex Petri dishes, and the dishes were decontaminated after use in a solution of 2% Amphyl/6% isopropanol for 24 hr and washed in 1% Liqui-Nox. Petri dishes, separated by gauze sponges, were wrapped with foil in groups of two or four and sterilized by autoclaving.

I claim:

1. Cells from the immortal human leukemia cell line MC-1010 (ATCC No. CRL-12253).

2. Modified MC-1010 cells comprising MC-1010 cells (ATCC No. CRL-12253) transfected with one more nucleic acid sequences.

3. Modified MC-1010 cells according to claim 2, wherein at least one transfected nucleic acid sequence encodes a protein that is expressed by the modified cell.

* * * * *